United States Patent [19]
Yugari et al.

[11] 3,985,617
[45] Oct. 12, 1976

[54] IMMOBILIZATION OF BIOLOGICALLY ACTIVE PROTEINS WITH A POLYPEPTIDE AZIDE

[75] Inventors: Yasumi Yugari, Kamakura; Yoshiki Minamoto, Chigasaki, both of Japan

[73] Assignee: Ajinomoto Co., Inc., Tokyo, Japan

[22] Filed: Oct. 29, 1974

[21] Appl. No.: 518,383

[52] U.S. Cl. .................................. 195/68; 195/63; 195/DIG. 11; 260/112 R; 260/112.5 R
[51] Int. Cl.$^2$............................................ C07G 7/02
[58] Field of Search................ 195/63, 68, DIG. 11; 260/112 R, 112.5 R

[56] References Cited
UNITED STATES PATENTS

| | | | |
|---|---|---|---|
| 3,574,062 | 4/1971 | Sato | 195/68 X |
| 3,705,084 | 12/1972 | Reynolds | 195/63 |
| 3,843,446 | 10/1974 | Vieth et al. | 195/68 |

FOREIGN PATENTS OR APPLICATIONS

| | | |
|---|---|---|
| 916,931 | 1/1963 | United Kingdom |

OTHER PUBLICATIONS

Julliard et al., Some Modifications of the Kinetic Properties of Bovine Liver Glutamate Dehydrogenase (NADCP) Covalently bound to a Solid Matrix of Collagen, FEBS Letters, vol. 14, No. 3, 1971, (pp. 185–188).
Zaborsky, O., Immobilized Enzymes, CRC Press, Cleveland, Ohio, 1973, (pp. 28–30).
Mitz et al., Synthesis of Biologically Active Cellulose Derivatives of Enzymes, Nature, vol. 189, 1961, (pp. 576–577).

*Primary Examiner*—David M. Naff
*Attorney, Agent, or Firm*—Hans Berman; Kurt Kelman

[57] ABSTRACT

Immobilized biologically active proteins such as enzymes having high activity and stability are prepared by covalent bonding of the biologically active protein to an azide derivative of a polypeptide such as polymethylglutamate of which at least one carboxyl group in a side chain is converted to a carboxyl azide group.

7 Claims, No Drawings

IMMOBILIZATION OF BIOLOGICALLY ACTIVE PROTEINS WITH A POLYPEPTIDE AZIDE

This application relates to immobilized biologically active proteins and to a process for preparing the same.

In enzymatic reactions, immobilized enzymes are superior to natural ones in their convenient recovery from the reaction mixtures. While many immobilization methods have been reported, most have shortcomings, such as low enzymatic activity of the immobilized products, weak bond strength between enzyme and carrier, or low mechanical strength of the products. Covalent bonding is superior to other immobilization methods in bond strength, but the enzymatic activity or mechanical strength of the known products is unsatisfactory.

It is an object of the present invention to provide immobilized biologically active proteins which retain a significant amount of their original biological activity.

In accordance with the present invention, there is provided a biologically active composition by contacting a polypeptide having repeating acidic amino acid units of which at least one carboxyl group in a side chain is converted to a carbonyl azide group and optional repeating units of a neutral and/or basic amino acid (polypeptide azide) with a biologically active protein having an amino acid unit including an amino group in position $\alpha$ or $\omega$, the biologically active protein being covalently bonded to the polypeptide azide through reactive groups.

The term "polypeptide azide" as used herein refers to a polypeptide having repeating units of the formulas (I) or (II), jointly represented by formula (Ia),

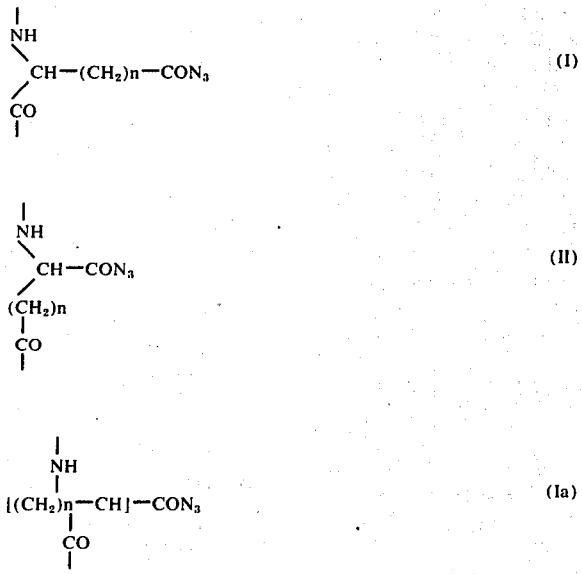

wherein n is 1, 2, 3 or 4.

The polypeptide azide usually has unreacted repeating units of the original polypeptide, of which the formulas are

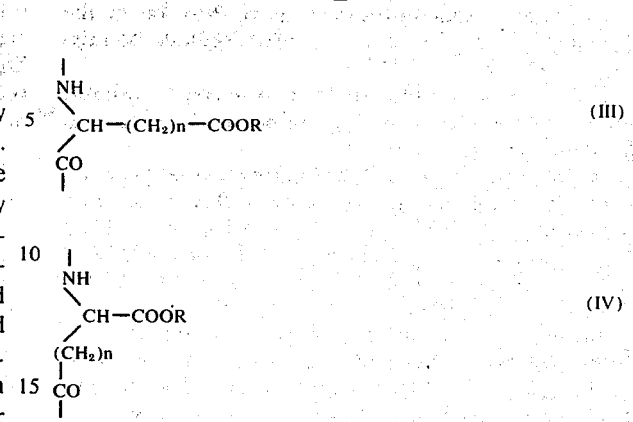

wherein n is as above, and R is hydrogen, lower alkyl having one to four carbon atoms, or metal.

When the polypeptide azide is prepared from polypeptide molecules having repeating units of formulas (III) or (IV) by the hydrazine method described below, some repeating units are cross linked with an adjacent polypeptide molecule through hydrazine, as shown by formulas (V), (VI) or (VII), and the cross-linking so produced remains in the polypeptide azide.

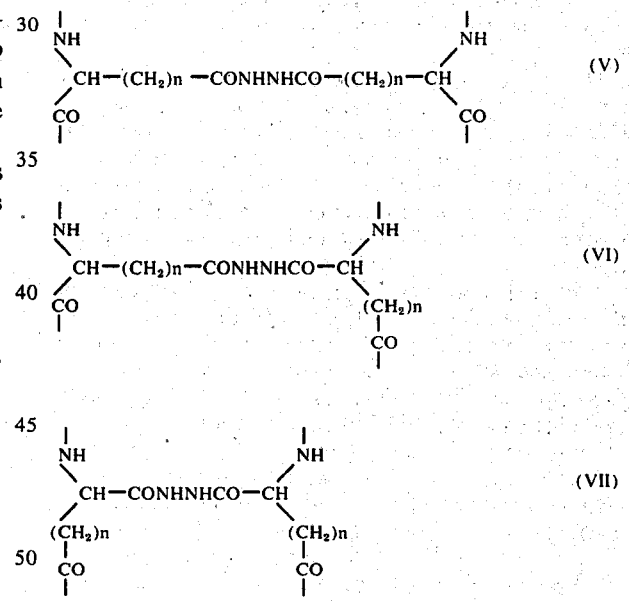

The advantages of this invention are also available in copolymers in which the above units are connected by peptide bonds to repeating units of one or more netural and/or basic amino acids in the backbone of the molecule. Repeating units of a neutral amino acid make the polypeptide water-insoluble.

The neutral amino acids which may link the repeating acidic amino acid units of Formulas (III) and (IV) in a peptide chain forming the backbone of the polymeric molecule include leucine, alanine, phenylalanine, serine, threonine, cysteine, methionine, and their derivatives, such as O-substituted hydroxy-amino acids and S-substituted sulfur-containing amino acids. Suitable basic amino acids are lysine, ornithine, arginine, histidine and their lower acyl derivatives.

The amino acids mentioned above may be in the optically active form, in the racemic form, or be mixtures of the two forms.

There are many methods for converting a carboxyl group to an acyl azide group, and most can be applied to the present invention.

In one of the most suitable methods, a polypeptide containing repeating units of a lower alkyl ester of an acidic amino acid is reacted with hydrazine, and the hydrazide produced is reacted with nitrous acid until the hydrazide groups in a portion of the units are converted to azide groups.

The homopolymers or copolymers which have repeating units of a lower alkyl ester of an acidic amino acid are prepared in any manner known, and the carboalkoxy groups in a portion of the units are converted to primary hydrazide moieties as described, for example, in Nature 189, p. 576 (1961), where it was reported that trypsin and chymotrypsin are immobilized on carboxymethyl cellulose whose carboxymethyl groups have been converted to azide groups. After the reaction with hydrazine, a portion of the units is usually cross-linked by the hydrazine, while other carboalkoxy groups remain unchanged.

The reaction product is separated from the reactant solution by filtration or centrifuging, washed with water until the washings are neutral, and, if desired, the product is further washed with a chilled, weakly acidic, aqueous solution and/or chilled aqueous solution of an organic solvent to remove most of the soluble constituents.

The washed product is immersed in 0.02 – 0.5 N mineral acid at a temperature below 20° C, preferably below 5° C, thereafter nitrous acid or an aqueous solution of a nitrite, for example, a 1–20% solution of sodium nitrite, is added to the mineral acid solution in one batch or within a few minutes, and the mixture is moderately stirred for 5 – 60 minutes at low temperature.

The polypeptide azide so produced is separated from the reactant solution, washed several times with chilled water and/or chilled buffer solution of a pH not to impair the activity of the biologically active immobilized protein. Thereafter, if desired, the polypeptide azide is further washed with a chilled aqueous solution of an organic solvent.

The weakly acidic aqueous solution which can be employed in the first washing process described above may be a dilute solution of a mineral acid, such as 0.01 N to 0.1 N hydrochloric acid or phosphoric acid. The mineral acid solution may contain an organic acid, such as acetic acid, or organic solvent which is water-miscible, such as methanol, ethanol, benzyl alcohol or dimethylformamide.

Suitable aqueous washing solutions of organic solvents include 10 to 70% (vol.) aqueous solutions of methanol, ethanol, ether, acetone, and dioxane.

A polypeptide azide may also be produced by reaction of a polyamino acid chloride with sodium azide.

The biologically active proteins to which the present invention is applicable include enzymes, such as urease, uricase, urokinase, amino acid acylase, aspartase, amylase, lipase, glucose oxydase and protease, natural proteins of animal and plant origin, and natural peptides, such as antigens, antibodies and peptide hormones.

These biologically active proteins may easily be immobilized by immersing a polypeptide azide in solutions of the proteins buffered to a pH at which the activity of the biologically active protein to be immobilized is not adversely affected, and whose temperature is kept below 40° C, preferably below 10° C, and by moderately stirring the mixture for 6 to 24 hours.

The polypeptide on which a biologically active protein is immobilized may have any shape and be a membrane, tube, fiber, porous shaped body, bead or viscous liquid.

In order to enhance the mechanical strength of the composition, the polypeptide may be deposited on various carriers. When the coated carrier is immersed in a solution, the coating may peel off unless fastened to the surface of the carrier by an adhesive. The adhesive may also fix water-soluble constituents of the polypeptide. Since the original polypeptide is usually a linear polymer and is appreciably water-soluble, some constituents which are only sparingly cross-linked and whose carboxyl groups are not fully converted to carboalkoxy groups may be dissolved even when combined with biologically active proteins.

Suitable adhesives include those capable of cross-linking, such as polyurethane resin, epoxy resin and polyester resin, and those incapable of cross-linking, such as polyvinyl chloride, polyvinyl acetate, polyvinylidene chloride, polyacrylate, and polyamide. Examples of such adhesives are reaction products of three parts by weight of polyurethanediisocyanate and one part by weight of epichlorohydrin, also reaction products of 3, 9-bis(3-aminopropyl)- 2,4,8,10 tetraoxospiro-[5,5]-undecane of the formula

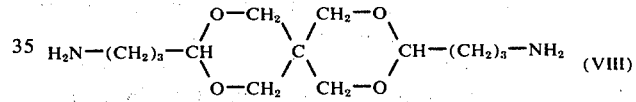

and epichlorohydrin.

The carriers capable of being coated with the polypeptide include beads of glass, synthetic resins, such as acrylic resin and vinyl chloride resin, or stainless steel, and the inner walls of glass and stainless steel tubes.

The adhesive is first applied to the surface of the carrier, a solution or a thin layer of the polypeptide is deposited on the coated surface, and the coating is dried. Alternatively, a solution of the polypeptide is first mixed with the adhesive, and the mixture is deposited on the surface of the carrier and dried. When a carrier is not used, the adhesive is still effective for fixing the water-soluble constituents of the composition and for increasing its mechanical strength.

The superiority of the present invention over known covalent bonding methods is demonstrated by the following two experiments.

EXPERIMENT 1

Small pieces of a copolymer of L-methionine and L-glutamic acid γ-methyl ester (mole ratio 1:1) weighing one gram were suspended in 10 ml methanol, 2 ml 80% hydrazine hydrate were added to the suspension, and the mixture was kept at 50° C for 2 hours. The hydrazide produced thereby was filtered off and washed four times with 50% methanol. Thereafter, the washed product was immersed in 30 ml of a mixture of equal volumes of methanol and 0.5 N hydrochloric acid, allowed to stand for a few minutes, and filtered off. The immersing procedure was repeated once more, the hydrazide product was washed with methanol and dried. The hydrazide weighed 0.8 gram and contained 1.1 meq/g hydrazino groups.

100 mg Hydrazide was suspended in 20 ml methanol cooled in an ice bath and 10 ml chilled 0.5 N hydrochloric acid, and then 2.0 ml chilled aqueous 3% sodium nitrite solution were added to the suspension. The mixture was stirred for 20 minutes at 0° – 4° C. The azide produced thereby was recovered by centrifuging at 3,000 r.p.m. for 2 minutes and washed three times with chilled 50% methanol and subsequently twice with chilled water.

The recovered azide was immersed in 3.0 ml chilled 0.1 M phosphate buffer solution of pH 8.7 containing 2.55 mg/ml urease and 1 mM EDTA, and the mixture was stirred at 4° C for 48 hours. The urease employed was produced by SIGMA Chemical Co. (Type III, 2,2 U/ml). The resulting composition containing immobilized urease was centrifuged off, and washed successively once with 0.05 M phosphate buffer solution of pH 7.0, twice with the same buffer solution additionally containing 1 M sodium chloride, and twice with the same buffer solution without sodium chloride. The total volume of the filtrate was about 45 ml. The urease activities of the immobilized enzyme and of the filtrate were 8.6 U (86 U/g carrier) and 8.0 U, respectively.

One unit of urease activity produces 1 mg nitrogen as ammonia from 0.25 M urea solution of pH 7.0 at 25° C in 5 minutes when the ammonia is colorimetrically determined by the indophenol method.

In a comparison test, the same urease was immobilized on a carboxymethyl cellulose in the manner described in Nature, 189, p. 576 (1961).

Carboxymethyl cellulose (CMC) was washed successively with water, sodium hydroxide, hydrochloric acid, methanol and ether, and dried. The hydroxyl groups of the washed CMC were converted to methyl ester groups in the conventional method, one gram of the methylated CMC was suspended in 10 ml methanol, 2 ml 80% hydrazine hydrate was added to the suspension, and the suspension was refluxed for one hour. The reaction mixture was allowed to stand for 2 hours at room temperature and centrifuged. The precipitated hydrazide was washed five times with methanol and dried.

100 mg Hydrazide was suspended in 10 ml 0.5 N hydrochloric acid cooled in an ice bath, and 2.0 ml chilled aqueous 3% sodium nitrite solution was added to the suspension. The mixture was stirred for 20 minutes, and then centrifuged at 3,000 r.p.m. for 2 minutes. The precipitate was washed three times with chilled 50% methanol and subsequently twice with chilled water.

On the carboxymethyl cellulose azide so produced, the urease was immobilized in the same manner as described above with reference to the copolymer of L-methionine and L-glutamic acid γ-methyl ester. An immobilized enzyme having 3.3 U (33 U/g carrier) of urease activity and a filtrate having 12.0 U of urease activity were obtained.

When the same urease was immobilized on polymethacrylic acid in the same manner as described with reference to CMC, the urease activities of the immobilized enzyme and of the washing solution were 1.4 U (14 U/g carrier) and 12.3 U, respectively.

EXPERIMENT 2

Azides of L-methionine-L-glutamic acid γ-methyl ester copolymer, of carboxymethyl cellulose, and of polymethacrylic acid were prepared in the same manner as in Experiment 1.

100 mg Batches of the three azide compounds were immersed each in 3.0 ml of chilled 0.1 M borate buffer solution of pH 8.5 containing 2.0 mg/ml of uricase, and stirred at 4° C for 48 hours. The uricase employed was yeast uricase having 2.86 U/mg of uricase activity. The resulting compositions containing immobilized uricase were centrifuged off, and washed successively once with 0.1 M borate buffer solution of pH 8.5, twice with the same buffer solution containing 1 M sodium chloride, and twice with the same buffer solution without sodium chloride.

The uricase activities of the immobilized enzymes and of the filtrates are shown in Table 1.

Table 1

| | Immobilized Enzyme | Filtrate |
|---|---|---|
| Copolymer | 14.4 U(144 U/g carrier | 2.2 U |
| CMC | 1.4 (14) | 12.4 |
| Polymethacrylic acid | 0.67 (6.7) | 13.7 |

To determine uricase activity, 0.1 – 0.2 ml of a sample containing about 5 – 30mU uricase was mixed with 5.0 ml of a 0.1 mM solution of uric acid in 0.1 M borate buffer solution of pH 8.5, and the mixture was stirred at 25° C for 5 minutes. In order to stop the enzyme reaction, 0.2 ml 20% trichloroacetic acid was then added, and the residual uric acid was determined colorimetrically at 292.5 mμ. One unit of uricase activity corresponds to 1 μmol of uric acid digested per minute.

EXPERIMENT 3

Several batches of filaments of poly-D-glutamic acid hydrazide were washed neutral with water on a filter having a bottom of sintered glass. Some batches were washed subsequently three times with 0.08 N hydrochloric acid, and thereafter again with water until the washings were neutral.

Hydrazide groups of the washed poly-D-glutamic acid hydrazide were converted to azide groups in the conventional manner at 4°– 5° C, and the reaction mixture was filtered through a glass filter. The azide on the sintered glass disk was washed three or four times with cold water, and in several instances subsequently three or four times with cold, 50% aqueous, organic solvent solution.

The poly-D-glutamic acid azide was immersed in 0.05 M phosphate buffer solution of pH 8.5 containing 1 – 3 mg/ml of acylase and in some instances 20% ethanol. The immobilization mixture was stirred by a magnetic stirrer or by shaking for 2 – 5 days at 4° C. The acylase-bearing solid was filtered off through a glass filter and washed with 0.05 M phosphate buffer solution of pH 7.0 – 7.2 until no acylase activity could be detected in the filtrate. The acylase activities of the immobilized enzyme and of the filtrate were determined in the following manner.

1.0 Ml of an acylase solution or of a suspension of a solid bearing immobilized acylase was added to 10.0 ml of a solution of 22 mM N-acetyl-DL-phenylalanine, 0.1 mM cobalt chloride, and 50 mM Veronal buffer solution of pH 8.0 at 37° C. The mixture was centrifuged for 1.0 minute, and a first sample of 0.2 – 0.3 ml supernatant was collected in a micropipette. The remaining mixture was stirred at 37° C for 30 minutes, and another sample of the same volume of supernatant was collected. Each sample was held for 5 minutes in water above 95° C to inactivate the acylase, and the phenylalanine present was determined by the colorimetric method of Yamm, Cocking, et al.

One unit of acylase activity produces one μmol of phenylalanine.

Table 2 lists, for each batch, the amount of poly-D-glutamic acid hydrazide filaments in terms of the poly-methyl-D-glutamate filaments from which the hydrazide was prepared, the use (+) or non-use (−) of 0.08 N HCl in washing the hydrazide filaments, the solvent used for washing the azide, the solvent used in the immobilization mixture, the initial amount of acylase, and the distribution of acylase between the filtrate and the immobilized enzyme.

zine hydrate with one volume pyridine for 1 hour at 50° C, and filtered off.

The polyglutamate hydrazide so produced was washed with water and three times with 50 ml 0.05 N hydrochloric acid. The washed hydrazide was immersed in 10 ml ice-cold 0.1 N hydrochloric acid for 15 seconds, 2 ml aqueous 3% sodium nitrite solution was added, and the mixture was stirred for 20 minutes. It was then filtered, and the solid material was washed several times with ice-cold 0.05 M phosphate buffer solution of pH 7.5, and several times with ice-cold 50% ethanol.

The azide so produced was shaken 48 hours at 4° C with 4 ml 0.05 M phosphate buffer solution of pH 8.5 containing 2 mg urease isolated from jack beans and having 5.6 U urease activity and 20% ethanol by volume. The reaction mixture was filtered, and the recovered solids were washed several times with ice-cold Table 2

| PMG Filaments mg | Hydrazide Washed with 0.08 NHCl | Azide Washing Solvent | Solvent in Immobilize'n Mixture | Initial Acylase U/ml | Acylase Recovered From Filtrate | Immob'd Enzyme Activity | U/g Carrier |
|---|---|---|---|---|---|---|---|
| 150 | − | Water | Water | 53U/1.5 ml | 87% | 7.5 U (14%) | 52 |
| 150 | + | Water | Water | " | 75% | 14 U (25%) | 93 |
| 150 | + | Dioxane 50% | Water | 130U/2 ml | 80% | 34 U (26%) | 231 |
| 150 | + | Ethanol 50% | Ethanol 20% | " | 77% | 44 U (34%) | 292 |
| 500 | − | Water | Water | 450U/10 ml | 93% | 13 U (3%) | 26 |
| 500 | + | Ethanol 50% | Ethanol 20% | " | 83% | 109 U (24%) | 218 |

EXPERIMENT 4

A film of poly-γ-methyl-D-glutamate having an intrinsic viscosity of 1.2 was cut into pieces 50 mm square and 32 μ thick, and the pieces were immersed in 100 ml of a hydrazine solution in an aqueous organic solvent (benzyl alcohol, N,N-dimethylformamide, or methanol) at 21° C. The hydrazide produced was filtered off, washed with water until free from hydrazine and solvent, and air-dried.

The hydrazide was analyzed for nitrogen content and methoxy group content (F. Viebock and C. Brecher), and the methoxy group content, hydrazide group content, and cross-linking group content were calculated and are shown in Table 3.

The Table shows the variation in the composition of the side chains due to the hydrazine concentration, to the nature of the solvent employed with the hydrazine, and the reaction time. All percentages are by weight.

Table 3

| Hydrazine Solution | | Reaction Time Hours | Side Chains, Mole % | | |
|---|---|---|---|---|---|
| %N₂H₄ | Solvent | | Hydrazide | Cross-linked | Methyl ester |
| 60 | 63% Benz.alc. | 1 | 49 | 14 | 37 |
| 60 | 63% Benz.alc. | 3 | 93 | 5 | 2 |
| 67 | 50% Benz.alc. | 1 | 35 | 21 | 44 |
| 67 | 50% Benz.alc. | 2 | 82 | 11 | 7 |
| 67 | 33% Benz.alc. | 2 | 42 | 32 | 26 |
| 67 | 33% Benz.alc. | 3 | 80 | 12 | 8 |
| 40 | 83% DMF | 6 | 28 | 49 | 23 |
| 60 | 63% DMF | 6 | 54 | 29 | 27 |
| 40 | 83% Methanol | 6 | 36 | 27 | 37 |

The following Examples further illustrate the invention. All percentage values and parts referred to in these Examples are by weight unless stated otherwise.

EXAMPLE 1

150 mg Poly-γ-methyl-D-glutamate film was immersed in 50 ml of a mixture of 10 volumes 80% hydra- 0.05 M phosphate buffer solution of pH 7.5 containing 1 M sodium chloride until no urease activity could be detected in the filtrate.

The activity of the immobilized urease was 4.3 U and that of the filtrate was 1.2 U when determined as in Experiment 1.

When the procedure described above was repeated, but without washing the hydrazide with dilute hydrochloric acid, without washing the azide with aqueous ethanol, and without adding ethanol to the urease immobilizing mixture, the urease activity of the immobilized enzyme was 2.0 U.

EXAMPLE 2

150 mg Poly-γ-methyl-D-glutamate filaments were treated with hydrazine and washed with water in the manner of Example 1, and then washed three times with 50 ml of 0.02 N hydrochloric acid.

The hydrazide was treated with nitrite and washed with 50% ethanol also as described in Example 1. The azide so produced was stirred 48 hours at 4° C with 4 ml 0.05 M phosphate buffer solution of pH 8.5 containing 4 mg jack bean urease having a urease activity of 11.2 U and 10% by volume acetone. The urease-bearing substance was washed as in Example 1, and the activities of the washed immobilized enzyme and of the filtrate were 9.8 U and 1.4 U respectively.

The urease activity of the immobilized enzyme was 2.7 times the activity of the enzyme immobilized in the otherwise identical procedure without washing of the hydrazide with dilute hydrochloric acid, without washing of the azide with aqueous ethanol, and without acetone in the urease immobilizing mixture.

EXAMPLE 3

Six parts poly-γ-methyl-D-glutamate, three parts polyurethane diisocyanate, and one part epichlorohydrin were dissolved in 300 parts ethylene dichloride. 10 g Porous glass beads of 80 – 120 mesh were stirred with 30 g of this solution, and the solvent was removed. The glass beads coated with the polyglutamate were dried at 100° C for 5 hours, and 1.0 g dried beads were immersed in a hydrazine solution to convert the poly-γ-methyl-D-glutamate coatings of the beads to the hydrazide as described in Example 1.

The beads then were washed with 0.08 N hydrochloric acid, treated with nitrite, and washed with cold 50% (vol.) acetone.

The azide coated beads were shaken 48 hours at 4° C with 1.5 ml of 0.05 M phosphate buffer solution of pH 8.5 containing 3.0 mg acylase (110 U) produced by Aspergillus, 20% by volume ethanol and 0.05 M sodium acetate and filtered off. They were washed thereafter with 0.05 M phosphate buffer solution of pH 7.5 containing 0.05 M sodium phosphate until no acylase activity could be detected in the filtrate.

The activity of the immobilized acylase was found to be 56 U (56 U/g), and that of the filtrate was 55 U.

The enzyme activity of the immobilized enzyme was 3.3 times that of the enzyme immobilized in the same procedure except for the washing processes. When the immobilized acylase was held at 70° C for 30 minutes, it retained 73% of its initial activity.

EXAMPLE 4

150 mg Beads (30 – 80 mesh) of a copolymer of DL-methionine and L-glutamic acid α-methyl ester (mole ratio 1:1) were treated with hydrazine and washed with dilute hydrochloric acid in the manner of Example 1. The hydrazide was treated with nitrite and washed with cold 50% (vol.) dioxane.

The azide bearing beads so produced were stirred 24 hours at 4° C with 2 ml 0.05 M phosphate buffer solution of pH 8.5 containing 3 mg jack bean urease having an activity of 8.4 U and 20% (vol.) ethanol. The beads carrying the immobilized urease were washed as in Example 1, and the activity of the washed immobilized urease was found to be 8.2 U (55 U/g). This was about 2.2 times the activity of the immobilized enzyme produced in the same procedure except for the washing processes.

When stored at 25° C for 6 months, the immobilized urease retained 91% of its initial activity.

EXAMPLE 5

A solution of 6 parts poly-γ-methyl-D-glutamate having an intrinsic viscosity of 1.2, 3 parts polyurethane diisocyanate, 1 part epichlorohydrin, and 300 parts of a solvent consisting of 9 volumes dichloroethane and one volume toluene, was stirred in an amount of 50 g with 10 g porous glass beads (80 – 120 mesh). The organic solvents were removed on a rotary evaporator, and the coated glass beads were dried at 100° C for 5 hours.

They were then immersed in 50 ml of a mixture of 10 volumes 80% hydrazine hydrate with one volume pyridine at 50° C for 3 hours.

The hydrazide bearing beads were filtered off, washed with water until free from hydrazine and solvent, and suspended in 100 ml chilled 0.1 N hydrochloric acid for 15 seconds. 15 ml Chilled, aqueous, 3% sodium nitrite solution was added to the suspension which was then stirred at 4° C for 20 minutes. The azide coated glass beads were filtered off, washed with ice-cold water and subsequently with 0.05 M phosphate buffer solution of pH 8.5, immediately immersed in 10 ml chilled 0.05 M phosphate buffer solution of pH 8.5 containing 30 mg jack bean urease having an activity of 63 U, and moderately stirred at 4° C for 24 hours. The glass beads were filtered off, and washed several times with 0.05 M phosphate buffer solution of pH 7.5 until no urease activity could be detected in the filtrate and subsequently once or twice with the same buffer solution containing 1 M NaCl.

The urease activity of the immobilized enzyme was 5.0 U/g and that of the filtrate was 12 U.

When the beads carrying the immobilized enzyme were packed in a column, and enzyme reactions were repeated at 25° C for 6 months using the column, the urease activity of the immobilized enzyme was scarcely lowered. The coating did not separate from the beads and was not eluted.

EXAMPLE 6

10 g Glass beads coated with azide modified polyglutamate were prepared as in Example 5, immersed in 5 ml of a solution of 10 mg Aspergillus acylase (650 U) in 5 ml 0.05 M phosphate buffer solution of pH 8.5, and further treated as described in Example 5. The acylase activity of the immobilized enzyme was 45 U/g and that of the filtrate was 190 U.

When the beads carrying the immobilized enzyme were packed in a column, and enzyme reactions were repeated at 37° C for 2 months using the column, the acylase activity of the immobilized enzyme was scarcely lowered and the flow rate did not change.

EXAMPLE 7

In the manner of Example 5, 60 g polyglutamate solution was deposited on 15 g alumina beads (100 – 200 mesh) and treated with hydrazine and nitrite. The azide bearing beads were immersed in a solution of 30 mg jack bean urease (70 U) in 20 ml 0.05 M phosphate buffer solution of pH 8.5, and further treated as in Example 5. The urease activities of the immobilized enzyme and of the filtrate were 5.3 U/g and 2 U, respectively.

When the beads carrying the immobilized enzyme wee stirred in a 200 ml beaker with a Teflon agitator of 3 cm diameter while an enzyme reaction was carried out for six hours, the urease activity of the immobilized enzyme was scarcely lowered, and neither separation nor elution of the coatings from the beads occurred.

EXAMPLE 8

30 g Glass beads of about 2 mm diameter were stirred with a glass rod in a mixture of 5 g 3% epichlorohydrin and 2 g 3% 3,9-bis (3-aminopropyl)-2,4,8,10 tetraoxospiro-[5,5]-undecane until the solvent was evaporated and the surfaces of the beads were almost dry.

The beads were stirred in 5 g of a mixture of dichloroethane and tetrachloro ethane containing 5% polymethyl-D-glutamate having an intrinsic viscosity of 1.8. When enough solvent was evaporated to make the mixture viscous, it was added little by little to a large amount of ethanol with stirring. After the addition was completed, the ethanol was removed, and the glass beads were dried at 100° C for 5 hours.

The glass beads coated with the polyglutamate were treated with hydrazine and nitrite, and reacted with acylase in the same manner as in Example 6. The activity of the immobilized acylase was 0.6 U/g. When the beads carrying the immobilized enzyme were packed in a column and employed for enzyme reactions, the acylase activity of the column was scarcely lowered and the flow rate of 10 cm/min did not change.

EXAMPLE 9

6 g 10% Epichlorohydrin was mixed with 2 g 10% 3,9-bis (3-aminopropyl)-2,4,8,10 tetraoxospiro-[5,5]-undecane. To the mixture, 2 g of a mixture of dichloroethane and tetrachloroethane containing 10% of polymethyl-D-glutamate having an intrinsic viscosity of 1.8 was added with stirring. The liquid then was sealed and allowed to stand at room temperature for 2 weeks. It became white, turbid, and very viscous.

It was stirred gradually into a large amount of methanol and then comminuted in a Waring blender (homogenizer) for 1 – 2 minutes. Methanol was evaporated, and the residue was dried at 100° C for 3 hours.

3 g White porous beads (30 – 100 mesh) produced in this manner were treated with hydrazine, and subsequently with nitrite, and reacted with acylase in the same manner as in Example 6. The acylase activity of the immobilized enzyme was 170 U/g. When the enzyme composition was packed in a column and employed for enzyme reactions at 37° C for one month, 92% of the initial acylase activity was retained and no difficulties occurred due to changes in the flow rate.

EXAMPLE 10

5 g 5% Polyvinyl chloride solution was mixed with 10 g 5% polymethyl-D-glutamate solution (intrinsic viscosity 1.8). A glass tube, 5 mm in inside diameter and 45 cm long, was coated internally with the solution. The solvent was evaporated while the tube was rotated, and then the tube was dried by heating at 80°– 100° C for 5 hours.

Using a small circulating pump, the polymethyl glutamate coating on the inner wall of the tube was treated with hydrazine and subsequently with nitrite. 5 mg (10.5 U) Uricase extracted from yeast was dissolved in 3 ml 0.1 M borate buffer solution of pH 8.5, the solution was injected into the glass tube, and the tube was rotated and shaken slowly at 4° C for 48 hours. The glass tube was washed in a conventional manner. The uricase activity of the immobilized enzyme was 9.3 U. When the inmobilized enzyme was employed for reaction with a passing substrate solution at a flow rate of 1 ml/min for 24 hours, its uricase activity was scarcely lowered and no elution of the coating occurred.

We claim:

1. A method of producing a biologically active composition which comprises contacting modified poly-γ-methyl glutamate including azide groups in repeating units of the formula

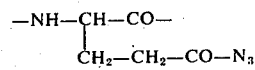

with an enzyme, said enzyme being a protein having an amino acid unit including an amino group in position α or ω, until an immobilized enzyme is formed by covalent bonds established by reaction between the azide groups of said modified poly-γ-methyl glutamate and said enzyme.

2. A method as set forth in claim 1, wherein said modified poly-γ-methyl glutamate is prepared prior to said contacting by immersing poly-γ-methyl glutamate consisting essentially of repeating ester units of the formula

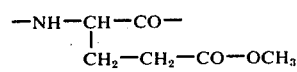

in an aqueous hydrazine solution until $OCH_3$ in a portion of said ester units is replaced by the hydrazide group $-NH-NH_2$, and immersing the hydrazide so formed in an aqueous solution of nitrous acid or a nitrite until said hydrazide group is converted to the azide group $-N_3$.

3. A method as set forth in claim 2, wherein said hydrazide prior to said immersing thereof in a solution of nitrous acid or a nitrite is washed with a weakly acidic aqueous liquid or with an aqueous solution of an organic solvent.

4. A method as set forth in claim 2, wherein said modified poly-γ-methyl glutamate prior to said contacting is washed with a weakly acidic aqueous liquid or with an aqueous solution of an organic solvent.

5. A method as set forth in claim 2, wherein said poly-γ-methyl glutamate is soluble in ethylene dichloride.

6. A method as set forth in claim 2, wherein said modified poly-γ-methyl glutamate, prior to said immersing, is deposited on an inert carrier.

7. A method as set forth in claim 6, wherein an adhesive is interposed between said carrier and the deposited modified poly-methylglutamate.

* * * * *

Disclaimer 3,985,617.—*Yasumi Yugari*, Kamakura, and *Yoshiki Minamoto*, Chigasaki, Japan. IMMOBILIZATION OF BIOLOGICALLY ACTIVE PROTEINS WITH A POLYPEPTIDE AZIDE. Patent dated Oct. 12, 1976. Disclaimer filed Feb. 4, 1977, by the assignee, *Ajinomoto Co., Inc.*

Hereby enters this disclaimer to claims 1 and 2 of said patent.

[*Official Gazette April 19, 1977.*]